(12) United States Patent
Sininger et al.

(10) Patent No.: US 6,200,273 B1
(45) Date of Patent: Mar. 13, 2001

(54) POWER-OPTIMIZED CUMULATIVE, SEQUENTIAL STATISTICAL METHOD FOR DETECTION OF AUDITORY EVOKED POTENTIALS

(75) Inventors: Yvonne S. Sininger, Fountain Valley, CA (US); Martyn Hyde, King City (CA)

(73) Assignee: House Ear Institute, Los Angeles, CA (US)

( * ) Notice: Subject to any disclaimer, the term of this patent is extended or adjusted under 35 U.S.C. 154(b) by 0 days.

(21) Appl. No.: 09/299,943

(22) Filed: Apr. 26, 1999

(51) Int. Cl.$^7$ ..................................................... A61B 5/00

(52) U.S. Cl. ................................... 600/559; 600/544

(58) Field of Search .......................... 600/544, 545, 600/559

(56) References Cited

U.S. PATENT DOCUMENTS

| | | | |
|---|---|---|---|
| 3,901,215 | 8/1975 | John | 128/2.1 B |
| 4,214,591 | 7/1980 | Sato et al. | 128/731 |
| 4,275,744 | 6/1981 | Thornton et al. | 128/731 |
| 4,462,411 | 7/1984 | Rickards | 128/746 |
| 4,493,327 | * 1/1985 | Bergelson et al. | 600/544 |
| 4,844,086 | 7/1989 | Duffy | 128/731 |
| 4,913,160 | 4/1990 | John | 128/731 |
| 5,003,986 | 4/1991 | Finitzo et al. | 128/731 |
| 5,230,344 | * 7/1993 | Ozdamar et al. | 600/544 |
| 5,601,091 | 2/1997 | Dolphin | 600/544 |
| 5,697,379 | 12/1997 | Neely et al. | 128/731 |

FOREIGN PATENT DOCUMENTS 195 48 982  7/1997  (DE).

OTHER PUBLICATIONS

Aoyagi, M. and Harada, J., "Application of Fast Fourier Transform to Auditory Evoked Brainstem Response", *Med. Inform.* (1988), vol. 13, No. 3, pp. 211–220.

Boston, J.R., Denault, L.G., Egol, A.B. and Snyder, J.V. "Objective Response Detection for Sensory Evoked Potentials", *IEEE Frontiers of Engineering and Computing in Health Care*, pp. 220–224.

Dobie, R.A. & Wilson, M.J., "Short–Latency Auditory Responses Obtained by Cross Correlation", *J. Acoust. Soc. Am.*, 76 (5), Nov. 1984, pp. 1411–1421.

Don, M., Elberling, C., and Waring, M., "Objective Detection of Averaged Auditory Brainstem Responses", *Scand. Audiol.* 13 (1984), pp. 219–228.

Elberling, C. and Don, M., "Quality Estimation of Averaged Auditory Brainstem Responses", *Scand. Audiol.* 13 (1984), pp. 187–197.

Friedman, J., Zapulla, R., Bergelson, M., Greenblatt, E., Malls, L., Morrell, F., and Hoeppner, T., "Application of Phase Spectral Analysis of Brainstem Auditory Evoked Potential Detection in Normal Subjects and Patients with Posterior Fossa Tumors", *Audiology* 23 (1984), pp. 99–113.

Herrmann, B.S., Thornton, A.R., Joseph, J.M., "Automated Infant Hearing Screening Using the ABR: Development and Validation", *Amer. J. Audio*, 4, pp. 6–14.

(List continued on next page.)

Primary Examiner—Cary O'Connor
Assistant Examiner—Charles Marmor, II
(74) Attorney, Agent, or Firm—Blakely, Sokoloff, Taylor & Zafman LLP

(57) ABSTRACT

A method for determining the statistical probability that an auditory brainstem response (ABR) to an acoustic stimulus is present in a human test subject. The method employs an algorithm that provides a continuously evolving estimate of the probability of ABR presence as acquired data accumulates. The algorithm utilizes a Hotelling $T^2$ test.

4 Claims, 6 Drawing Sheets-

OTHER PUBLICATIONS

Mason, S.M., "Automated System for Screen Hearing Using the Auditory Brainstem Response", *Brit J. Audiol.*, 22 (1988), pp. 211–213.

Moser, J.M., and Aunon, J.I., "Classification and Detection of Single Evoked Brian Potentials Using Time–Frequency Amplitude Features", *IEEE Trans Biomed Eng., MBE—33*, (1986), pp. 1096, 1106.

Özdamar, Ö., Delgado, R.E., Eilers, R.E., and Widen, J.E., "Computer Methods for On–Line Hearing Testing with Auditory Brain Stem Responses", *Ear Hear*, vol. 11, No. 6 (1990), pp. 417–429.

Valdes–Sosa, M.J., Bobes, J.A., Perez–Abalo, M.C., Perera, M., Carballo, J.A., and Valdes–Sosa, P., "Comparison of Auditory–Evoked Potential Methods Using Signal Detection Theory", *Audiology*, vol. 26, 1987, pp. 166–178.

Wicke, J.D., Goff, W.R., Wallace, J.D., and Allison, T., "On–Line Statistical Detection of Average Evoked Potentials: Application to Evoked Response Audiometry (ERA)", *Electroenceph Clin Neurophysiol*, vol. 44 (1978) pp. 328–343.

Wilson, J.J. and Dobie, R.A., "Human Short–Latency Auditory Responses Obtained by Cross–Correlation", *Electroenceph Clin Neurophysiol*, vol. 66 (1987) pp. 529–538.

Picton, et al., *Reliability Estimates for Steady–State Evoked Potentials*, Electroencephalography and Clinical Neurophysiology, vol. 68, no. 2, Mar. 1987, pp. 119–131.

Hotelling, et al., *Analysis of a Complex of Statisical Variables into Principal Components*, J. Educational Psychology, APA, vol. 24, 1933, pp. 417–441.

* cited by examiner

POWER-OPTIMIZED CUMULATIVE, SEQUENTIAL STATISTICAL METHOD FOR DETECTION OF AUDITORY EVOKED POTENTIALS

BACKGROUND OF THE INVENTION

1. Field of the Invention

The present invention relates generally to the field of assessing hearing capacity in humans. More particularly, the invention is a method for quantifying the probability that an auditory brainstem response (ABR) is present in an electrophysiologic recording from a human infant.

2. Background of the Invention

The ABR is a waveform of fluctuating electrical potential over time, which may occur in response to a brief, transient acoustic stimulus such as a click. The ABR originates in the neurons of the auditory nerve and its higher connections in the brain stem. When recorded from electrodes on the scalp or neck, it is less than one microvolt in size, and is obscured by much larger ongoing random potentials that arise elsewhere in the brain and the musculature of the head and neck. Computer summation or averaging of the responses to several thousand stimuli presented at rates typically in the range of 20–50 per second is required to enhance the ABR "signal" relative to the background electrical "noise", and to render it visually detectable in the summed or averaged response.

The presence or absence of an ABR for a specific type and intensity of stimulus can be used as a proxy for overt behavioral response, indicating whether or not the stimulus was audible. This is the basis for an electrophysiologic hearing screening test, of particular value in subjects such as infants who are unable to give reliable, behavioral responses to sound.

In the newborn population, it is widely acknowledged that it is important to detect and manage hearing loss as early as possible, and preferably in the first six months, to facilitate development of speech, language and cognitive skills. In 1993, the National Institute on Deafness and Other Communication Disorders sponsored a Consensus Conference on Early Identification of Hearing Impairment in Infants and Young Children. That conference recommended screening for identification of hearing impairment in the newborn period for all infants regardless of the presence or absence of risk factors for hearing loss, that is, universal infant hearing screening. These recommendations were endorsed and reiterated soon after by the American Academy of Audiology and the Joint Committee on Infant Hearing, 1984. Many states have recently implemented, or are in the process of implementing, such screening programs. This widespread endorsement of mass hearing screening of neonates and infants has created a challenge for scientists and clinicians to have fast and accurate tools ready for evaluating potential hearing loss in infants.

ABR testing is well established as a core part of most screening protocols. The clinical utility of ABR-based hearing screening tests depends critically on the accuracy of the ABR detection decisions. Such decisions are intrinsically prone to error, because they involve the detection of a signal in random noise that may obscure a genuine signal or masquerade as a signal when none is present. False-positive ABR detection leads to a false-negative screening test: the hearing-impaired child passes the screening test and receives no intervention. Other manifestations of disorder may be ignored, given that the test was passed, so the screening does active harm. False-negative ABR detection tests cause false-positive screening tests; this precipitates needless follow-up diagnostic assessment costs, as well as indirect costs of mislabeling a normal child.

A distinction must be drawn between detection tests that are empirical and those that are analytic. Empirical tests are based upon experimental studies of the distributions of a given test statistic when response is thought to be present or absent. Usually the determination of response presence or absence is based on expert subjective assessment of the average records obtained in a set of subjects. There are two major difficulties with this approach. First, the expert judgments may be wrong, which clearly confounds the assessment of the accuracy of the test statistic. Second, there is no proof that the results observed in one set of subjects will necessarily apply to a different set of subjects or to a situation in which any feature of the data recording or analysis is changed. This is a failure of generalizability of the empirical validation process.

Analytic methods, in contrast, do not appeal to experimental validation datasets. They are based upon known properties of known statistical distributions relating to the chosen test statistic. Thus, rather than relying on empirical experimental data, analytic methods capitalize upon the vast body of statistical distribution theory and statistical tables of distributions. It is necessary to show that real data satisfy certain assumptions that are required for certain distributions to pertain, but these assumptions may be weak, easily satisfied, and easily proven to hold. Such methods are both highly quantitative, yielding known and specifiable rates of decision error, and are also highly generalizible across datasets and measurement conditions.

A crucial characteristic of a good statistical response detection test is that it has the highest possible statistical power. Power is the probability that the test will correctly detect a response that is genuinely present. Less than optimal test power is very disadvantageous in practical terms. A loss of power translates directly to longer test time than necessary to reach the statistical criterion for response detection. This is a major practical disadvantage because some babies yield satisfactory measurement conditions for only brief periods of time, they may be untestable due to test inefficiency. Also testable babies will take longer to test than necessary which increases costs and decreases throughput. This factor will be especially crucial in light of the implementation of universal newborn hearing evaluation protocols now mandated in many states. Third, the use of a test that is less powerful than necessary will result in larger rates of detection decision error than would be possible with a more powerful test.

Prior Art Detection Systems

Current approaches to automated detection of ABRs include techniques that evaluate the time-domain waveform and those that assess spectral characteristics (frequency domain). Automated detection of neonatal click-evoked ABR to low-level stimuli for mass screenings have primarily involved analysis in the time domain, although one known system includes both time and frequency domain analysis. At present, four systems have been used or sold as "automated infant ABR screening" devices. By that we refer to those devices in which decisions regarding ABR presence or absence or test "Pass" or "Fail" (sometimes called "Refer") is made by the system itself (not by the examiner) based on some predetermined criteria that are discussed below.

The general approach of the detection algorithm employed by the most commonly used system for automated ABR detection in infants appears to be as follows: A set of sample points are weighted according to their relative magnitude in the standard infant ABR waveform. It is not clear how the position or number of the data points are selected. The polarities of the amplitude of each point in a standard or template are compared with those observed at the corresponding latency in each sweep during averaging. Each time a sweep is sampled, the correspondence of polarity between the data and the template at each of the selected time points yields a count of +1. After every 500 sweeps, the template points are shifted in increments of 0.25 ms over a 3 ms range to locate the position of maximum polarity correspondence. Presumably, this is done using an accumulated average of some kind, but this is not clear. Each sample in each sweep constitutes a trial and running counts of the numbers of polarity matches and trials are accumulated. Because the probability of a polarity match for each point is 0.5 if the response is absent, a quantitative hypothesis test can be constructed based on a binomial model. This technique appears to be a combination of template cross-correlation with a multi-point amplitude-based detection criterion after a one-bit conversion.

The detection algorithm used in this system is statistically based but is far from analytic. Specific disadvantages are as follows:

Lack of validity: The algorithm effectively counts the number of times the polarity of the recorded activity matches the expected polarity of an ABR template waveform. Several points are tested per sweep and the number of polarity coincidences is also summed over many sweeps.

Because the successive data points within each sweep are not statistically independent, the sampling distribution of the number of coincidences will not have the binomial distribution that is assumed. This means that the actual error rates of the test are not represented accurately in statistical tables. Therefore, the method is substantially empirical. Actual error rates may only be determined by experiment with quantitivity and generalizability limitations noted earlier.

Power Sub-optimality: This detection algorithm counts correspondence events between observed and expected polarity of activity at specific times. The actual amplitude of the observed signal is not fully utilized, only the polarity. An analogy can be drawn to the use of the Ordinary Sign Test instead of the Student t-test to examine the hypothesis that the true mean of a sample of n observations is zero. The sign test uses only the polarity of the data, whereas the t-test, which is the most powerful test possible under the assumption of normal error distributions, uses all of the amplitude information. The asymptotic relative efficiency of the sign test is 2/pi, or 64%. This implies that any sign-based detection method will sustain a substantial loss of power.

Another commercially available instrument for ABR hearing screening includes automatic detection that is based on the following algorithm: For any particular stimulus level, the system acquires two ABRs with a fixed stimulus level. The averages are stopped if the estimated signal-to-noise ratio exceeds one or after 1,024 sweeps. If both averages have SNR>1, the response is deemed present. If not, a cross correlation analysis is performed. The latency region of 5 to 12.5 ms post-stimulus is sectioned into seven overlapping 'windows', each of 2 ms duration. For each window position, a Pearson correlation coefficient of the data values in the two averages for each and every successive time point in the given window is calculated. The test variable is the maximum absolute value among the seven correlations covering all window positions. If the test variable exceeds 0.9, the ABR is deemed to be present. This approach to automatic detection is an adaptation of a simple, correlation-based detection method first reported for the ABR by Weber, B. A and Fletcher, G. L., 1980 A Computerized Scoring Procedure for Auditory Brainstem Response Audiometry. *Ear and Hearing,* 1, 233–236. (1980).

The detection algorithm of this device is highly empirical. The primary detection statistic is a cross correlation coefficient between two independent averages using the region of anticipated response. The test statistic is the absolute maximum of the observed correlations. Because of the extensive correlation (autocorrelation) between successive data values in each of the averages, the statistical distribution of the test statistic is unknown, and detection error rates cannot be derived from statistical tables. The critical values for the test statistic, and the error rates, can only be estimated by experiment. Indeed, they were selected using empirical data with expert subjective judgment as the gold standard for response presence or absence. The serious limitations of this method were described earlier.

Details of response detection in a third prior art system are proprietary, although the manufacturer has released a non-detailed description of the decision-making system. Briefly, the system evaluates three aspects of the infant ABR in the decision process. First, the system determines presence or absence of an ABR in a record by evaluating (a) the presence of a predetermined spectral component of the response, using a multivariate analysis simultaneously assessing both real and imaginary components of a specified Fourier component and (b) an $F_{SP}$-like signal to noise estimate. If those criteria are met, the waveform morphology is checked with a type of template match that evaluates certain features of the waveform (peak number and placement). It appears that all three aspects of response detection algorithm must be satisfied for an infant to receive a "pass" from this system.

Limited information is available about this proprietary detection algorithm. It is based on a combinatorial approach using four types of measure: template (wave shape) and non-template features in both the time and frequency domains. The frequency domain algorithm involves examining the distribution of sine and cosine parts of several harmonics of the Fourier spectrum of the recorded activity, and a comparison with the expected values for both noise and ABR signals. This is combined in an unknown manner with a "modification of the so-called $F_{SP}$ technique". The detection stage is followed by a verification stage that examines the extent to which the detected and estimated waveform matches expected waveshape characteristics.

The performance of this approach is not known and not derivable from statistical distribution theory. The multi-component nature of the method virtually guarantees that it is not of analytic strength, but that it will be empirical. An alleged advantage is its exploitation of both time-domain and frequency-domain features. This is highly questionable, because the time-history and Fourier spectrum of any activity are linear transformations of each other and contain identical underlying information.

$F_{SP}$

A fourth prior art technique that has been applied to infant ABR detection for screening is the $F_{SP}$ (This technique is described in Elberling, C. & Don, M. (1984). Quality Estimation of Averaged Auditory Brainstem Responses. *Scand Audiol,* 13, 187–197 and Don, M., Elberling, C. & Waring, M. (1984). Objective Detection of Averaged Auditory Brainstem Responses. *ScandAudiol* 13, 219–228.). This technique is not applied commercially for specific use in infant screening but is available on some commercial evoked potential systems for general use (Neuroscan and Nicolet "Spirit") and was applied to automated newborn hearing screening by the first named inventor of the present invention in a multi-center study funded by the National Institute on Deafness and Other Communication Disorders. $F_{SP}$ involves calculation of a variance ratio (hence the F) the numerator of which is essentially the sample variance of the average and the denominator of which is the variance of the set of data values at a fixed single point (hence the "SP") in the time window across a group of sweeps.

$F_{SP}$ is used to estimate the "quality" or the signal-to-noise ratio of an auditory evoked potential. Calculation of $F_{SP}$ is based on the fact that any ABR recording is background noise (random brain and muscle activity not related to the auditory signal) and, if the signal is audible to the subject, each recording also contains neural activity from the auditory system that is systematic in scalp recorded morphology and time-locked to the onset of the eliciting auditory signal. For any given single, digitized time point in the averaged ABR waveform, the neural contribution to the amplitude measured at that point is constant from sweep to sweep whereas the noise contribution to amplitude should be random. Consequently, the neural response will contribute nothing to the variance of the amplitude at any single point and the sweep to sweep variance of a single point in the analysis window can be used as an accurate estimator of the variance of the background noise in the recording. This is referred to as VAR(sp).

Calculation of $F_{SP}$ is illustrated in FIG. 1. The magnitude of the averaged response can be characterized by the point to point variance of the digitized amplitude measures for a specified window of the average. In the standard $F_{SP}$ calculation, each point across a specified time window is used in a standard variance calculation referred to as VAR(s). This value is comprised of the energy of the ABR (if present) as well as the energy of the averaged noise. Every 256 sweeps the averaging process is halted momentarily and VAR(s) and VAR(sp) and the ratio of the two ($F_{SP}$) is calculated. The numerator or VAR(s) includes signal and noise and the denominator or VAR(sp) estimates noise. When no signal (ABR) is present the expected value of the ratio is close to 1. The ratio of variances has the known statistical F distribution, indexed by a parameter known as the degrees of freedom (dof). Consequently, when the degrees of freedom are known, the probability of false positive detection for any $F_{SP}$ value associated with an evoked potential recording can be determined by look up on an F table.

In a standard paradigm, $F_{SP}$ values are updated after each 256 sweeps. As the averaging process reduces background noise, the $F_{SP}$ value associated with a recording containing a true ABR, will grow. A priori rules can be established for halting of the averaging process based on a comparison of achieved and desired probability of true response detection. For example, in the article cited above, Elberling and Don, (1984) used a conservative estimation of degrees of freedom and determined that $F_{SP}$ of 3.1 would correspond to true-positive detection confidence of 99%. In that case, the $F_{SP}$ value was used as the stopping criterion for the averaging process, indicating that the desired signal to noise ratio had been achieved. Because any given recording or subject will vary dramatically in the level of the background noise and the amplitude of the evoked potential, using a target $F_{SP}$ as a stopping rule optimizes the use of averaging time, averaging shorter periods of time in good SNR and longer in poor SNR conditions.

The disadvantages of the $F_{SP}$ technique include:

Excessive window length: The standard response analysis window has length 1000/HPF ms where HPF is the high-pass cutoff frequency of the recording amplifier. For a typical case of HPF of 100 Hz, the length is 10 ms. This is generally greater than the length of the region of significant response amplitude. Thus, time regions that contribute little or nothing to the numerator variance estimate are included. This reduces the expected value of the numerator, resulting in a less sensitive test (a test with lower statistical power) than if the window were delimited to regions of substantial response amplitude.

Sub-optimal test points: Even given a response-focused window, some time points within the window contribute more to the response variance than do others. In general, there will exist some subset of all the points in the window that develops maximum variance for a given response waveform, and there will be many other subsets that develop variance substantially greater than the variance of the entire window. It follows that even for a focused window, to select all points in the window as is done in the standard $F_{SP}$ is sub-optimal with respect to statistical power. Both of these disadvantages result in a detection test that is less powerful than necessary.

Conventional $F_{SP}$ can be classed as semi-empirical or semi-analytic. The approach is vastly more quantitative and reproducible than is subjective judgment of response presence or absence. The limitation arises from the fact that the statistical degrees of freedom in the numerator variance estimate are known only approximately. This is due to the fact that the effective degrees of freedom in a time series that has correlation between successive data points, as is the case for ABR data, are not equal to the number of data points used in calculating the variance estimate. For example, a time window containing 100 data points is normally assumed to have 99 degrees of freedom, but may actually only have 10. This means that the distribution of the sample variance of such a set of points will follow chi-square with 10 dof, not chi-square with 99 dof. The distribution of the $F_{SP}$ statistic will change accordingly. Experimental studies have shown that the effective dof in, say, a 10 ms window of ABR data vary slightly across subjects and measurement conditions. Since the dof in a individual subject are not known exactly, but rather, only approximately, the Type I error rate (alpha, the significance level of the response detection test) will be only approximately correct.

Thus a great strength of $F_{SP}$ is that the F-distribution is valid. The qualification is that the decision error rates are not known exactly, only approximately.

SUMMARY OF THE INVENTION

The subject invention provides a method for determining the statistical probability that an ABR to an acoustic stimulus is present in a test subject. This allows the technician to make detection decisions that are valid, consistent and efficient, and which have known and specifiable rates of error. These features offer substantial advantages over current methods, and are especially important in the design of effective and cost-efficient large-scale public health screening programs for infants.

The invention employs a computational algorithm that provides a continuously evolving estimate of the probability of ABR presence as acquired data accumulates. It may be used to determine response probability and to govern when to stop the data acquisition. The algorithm offers substantial improvements over the best available semi-analytic method, namely $F_{SP}$. In particular, the algorithm employed by the present invention improves the power and efficiency of response detection and improves the degree to which the Type I error rate (alpha) and the power can be specified and controlled.

The algorithm utilizes the Hotelling $T^2$ test. New features are:

i. Application of a $T^2$-based test to time-domain evoked potential data.

ii. Application of time-domain $T^2$ in a cumulative, sequential manner.

iii. The incorporation of a quantitative strategy to define the target epoch, based on the relationship between non-centrality, degrees of freedom and epoch length.

iv. The test is completely analytic, with known degrees of freedom, and avoids any appeal to empirical normative data. It provides exact and valid error rates and power.

DETAILED DESCRIPTION OF THE INVENTION

Figure 1:
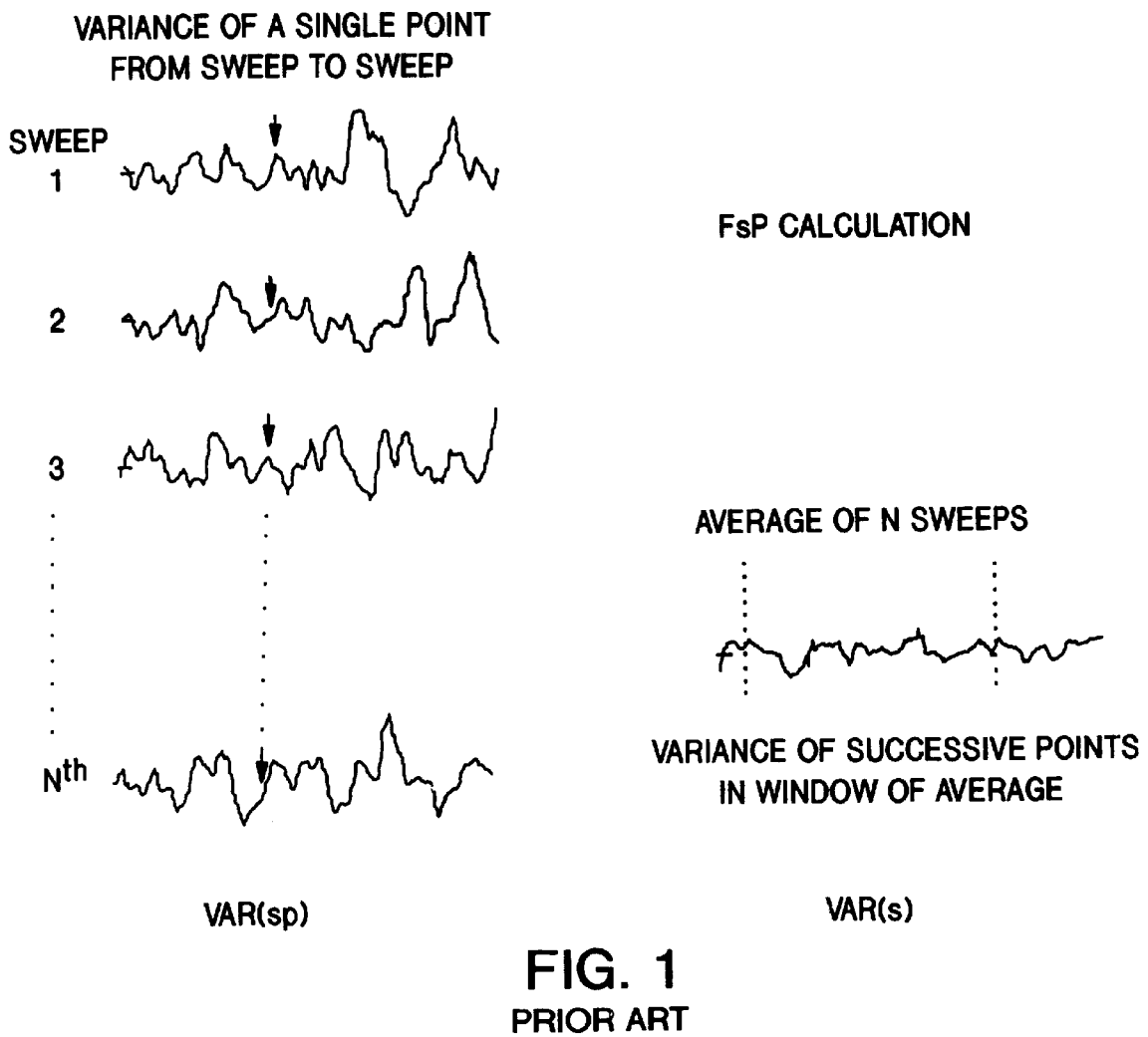
FIG. 1 illustrates prior art calculation of a $F_{SP}$ statistic for ABR waveforms.

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail. The invention set forth herein may include elements of the well-known methods and devices disclosed hereinabove.

Power-Optimized Time-Domain Cumulative Sequential Hotelling $T^2$ Test.

It was noted earlier that one limitation of the standard $F_{SP}$ test is its semi-analytic nature, which stems from the uncertainly about the true degrees of freedom of the test statistic in any specific test case. The present invention employs a Hotelling $T^2$ statistic. This is not a variance ratio test like $F_{SP}$. Rather it is a test of the joint-zeroness of the ABR data average, again at various selected time points post-stimulus. The Hotelling transform is described generally in "Analysis of a Complex of Statistical Variables into Principal Components", Hotelling, H. (1933), *Journal of Educational Psychology*, Vol. 24, pp 417–441.

For any target signal, it is clear that non-zeroness of the signal will tend to cause non-zero variance over time. However, it is obvious that, for example, if the signal is constant over the domain of interest, a test of zeroness may be positive but a test of variance will not be. (The variance of a constant being zero.) Thus, the statistics employed by the two embodiments of this invention address related but different facets of signal morphology, the details of which have not heretofore been explored systematically.

In the case of a time-variant waveform such as the ABR, the $T^2$ and the $F_{SP}$ tests access both conjoint and disjoint waveform features. The unique advantage of the $T^2$ test is that it is completely analytic. It is also the most powerful of all tests of joint non-zeroness of multiple data items. It is highly robust, maintaining correctness of significance levels even in the face of large departures from normality (Gaussianity) of source data. In practice, ABR data are approximately normally distributed or can easily be transformed to be so.

The analytic nature of $T^2$ stems from its intrinsic ability to take account of any pattern of correlation (covariance) among the data points. The sample variance-covariance matrix for the k-point data vector is incorporated into the statistic. This avoids any need to estimate or assume the degrees of freedom.

The $T^2$ statistic is well known in domain of multivariate statistical analysis. However, it has not heretofore been applied to time-domain ABR data. The standard view of ABR data is as a time-series; this is totally different from the multivariate viewpoint, which treats the data vector as a single realization or data point, in a vector space of k dimensions. There has been a report of a very restricted $T^2$ application to the two components of a single harmonic in the Fourier spectrum of the ABR. This would, however, function very poorly as a response detection test, because the information contained in the time-domain ABR is distributed among many Fourier components; to focus on a single component would sustain massive power loss, rendering the technique completely unsuitable for response detection in a mass screening context. In fact, the single-harmonic application of the $T^2$ test is both trivial and a misnomer: the two components (real and imaginary, sine and cosine) of any Fourier harmonic are in fact statistically independent, vitiating the entire point of the $T^2$ approach, which is to accommodate covariance among the data items. For the 2-component independent-measure problem, the $T^2$ statistic degenerates to a simple chi-square statistic.

There are two other important features of the $T^2$ statistic as employed by the present invention. The first is that the power of the $T^2$ test is diluted, as is the power of standard $F_{SP}$, if the selected set of data items is not carefully focused on the target waveform. In the present invention, this focusing and power enhancement is achieved by defining a putative response region in terms of the mean square response energy per unit time. Regions of low energy are not included.

Secondly, the application of the $T^2$ test to ABR detection in the time domain is done in a manner that is completely different to other multivariate applications. Normally a sample of (multivariate) data items is collected and the $T^2$ test applied to the entire sample. In this application, there is an acute need to stop data acquisition as soon as possible, consistent with achieving satisfactory decision error rates. The amount of data required varies dramatically over subjects, depending primarily on the amplitude of the electrophysiologic "noise" that obscures the genuine ABR. The approach to this problem is to apply the $T^2$ test in a sequential manner, to the accumulating dataset. Data acquisition is terminated when the response is detected, when the residual noise in the average record reaches a predetermined low value, or failing that, when a preset maximum number of sweeps is acquired. This iterative, cumulative sequential method of applying the $T^2$ test is unique.

The $T^2$ statistic used in the technique of this invention has the form:

$$\frac{N-k}{k(N-1)} \cdot N(\bar{x} - \mu_0)' S^{-1} (\bar{x} - \mu_0)$$

where
- N is the number of sweeps
- k is the number of selected test points
- $\bar{x}$ is the average data vector for the k points
- $\mu_o$ is the population mean vector under the null hypothesis, which for ABR testing is the null vector, and
- $S^{-1}$ is the inverse of the k×k covariance matrix This statistic has the (central) F distribution with k and N-k dof, when the ABR is absent. When response is present, the distribution is non-central F, with k and N-k dof and non-centrality parameter:

$$\tau' \sum\nolimits^{-1} \tau$$

where τ is the true response ABR vector at the k selected time points and $\Sigma^{-1}$ is the inverse of the population variance-covariance matrix (of which S is an estimate).

Figure 2A:
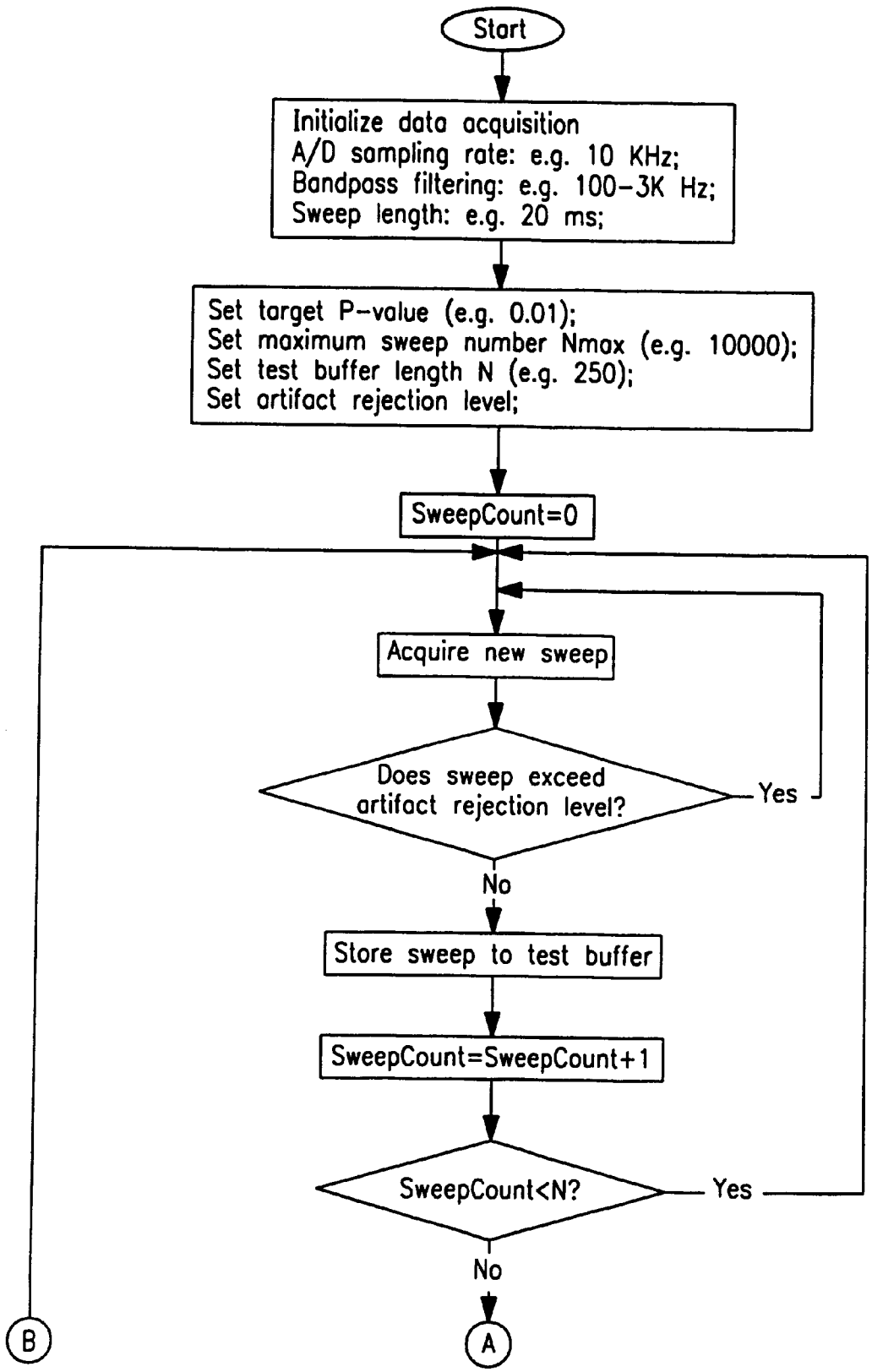
FIGS. 2a, 2b is a functional flow diagram of the diagnostic procedure of the invention.
Figure 2B:
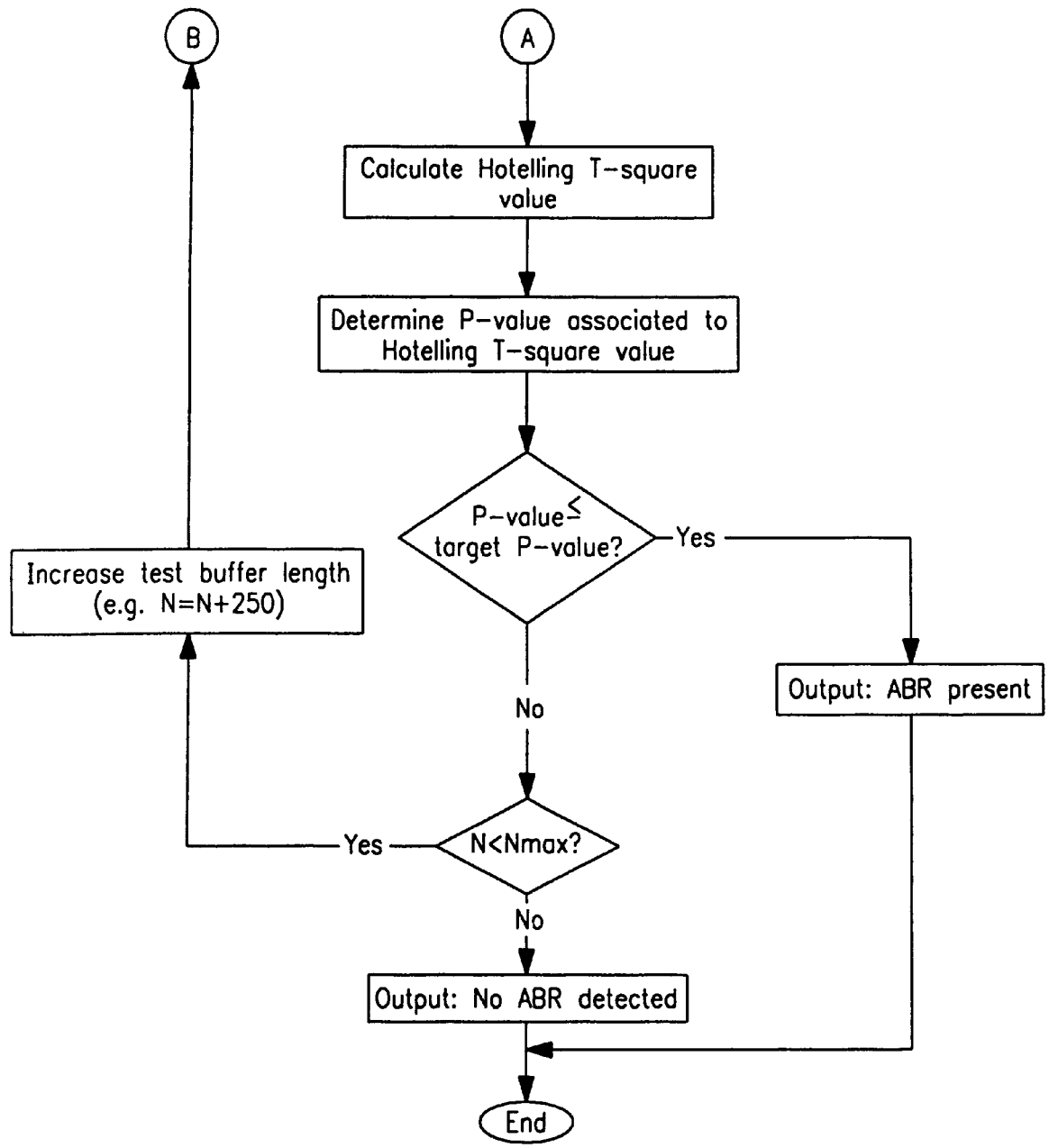

FIGS. 2a, 2b is a flowchart of the screening test in accordance with the second embodiment of this invention. The procedure begins with routine setting of acquisition parameters for the A/D converter including sampling rate appropriate for ABR and data filtering etc. In the example used, 20 ms of activity is digitized at 10,000 Hz (200 points). At this time the technician also decides the target P-value for the test. For example, a P-value of 0.01 indicates 99% confidence that the ABR detected is an actual response. The maximum number of sweeps is selected, which indicates how long the testing should continue before stopping. The test buffer length is also referred to as the block size. This is the sub-sample of sweeps between each recalculation of the test statistic. Artifact rejection level is a voltage level. Because unwanted activity such as muscle responses, have very large voltage relative to the neural response, any sweep containing very large excursions is not used to avoid excessive contamination of the data.

Figure 3:
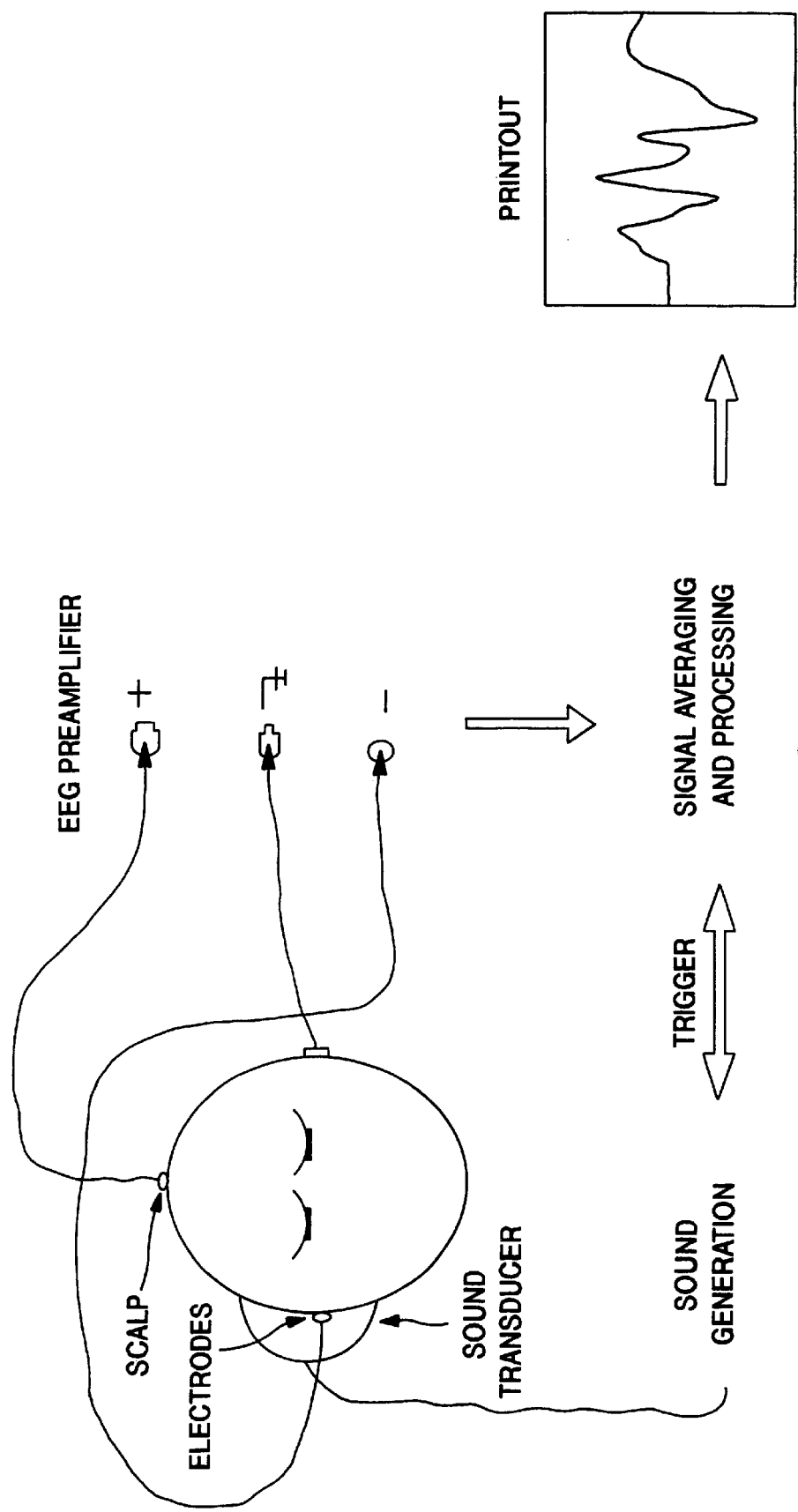
FIG. 3 diagrammatically illustrates the electrophysiologic data recording procedure of the present invention.

The acquisition of each sweep of EEG is accomplished using standard techniques. A schematic of the instrumentation is shown in FIG. 3. EEG activity is acquired by means of scalp-applied, metal disk electrodes connected by lead wires to a differential preamplifier. The preamplifier subtracts signals recorded from two scalp placements to eliminate like components of the recordings assumed to include noise (activity other than neural evoked potentials). Placement of these electrodes should be carefully chosen to optimize the recording of target waveforms. For example, the positive lead at the vertex (Cz) and negative at the hairline on the back of the neck or mastoid will be optimal for recording an infant ABR in response to low-level signals. A two-channel recording may be employed. Signals are amplified and band-pass filtered with filter specifications chosen specifically to enhance the target activity.

EEG activity is sectioned into epochs or sweeps of user-determined duration, for example 10–30 ms. Activity is digitized with a sampling rate appropriate for the spectral content of the signal. A triggering mechanism is used to synchronize the sampling of each sweep and the presentation of appropriate auditory stimuli with a user-selected inter-stimulus interval. The stimulus is generally a 100 μs square-wave pulse that produces a click when applied to the appropriate transducer.

With reference again to FIG. 2, as each block of sweeps is collected, the calculation of the test statistic takes place. The associated P-value is then determined and compared to the target P-value initially set by the technician. If the target is not reached, the entire process repeats. Recording is halted when response presence or absence is determined in accordance with the target P-value. The device may or may not have a hard-copy printout of response, or may have a more simplified indicator of the response decision such as "pass" or "fail".

Experimental results

Twelve, healthy newborns were evaluated at the Infant Auditory Research Laboratory of Los Angeles County +University of Southern California Medical Center, Women's and Children's Hospital. One or both ears were assessed by standard ABR techniques using both 30 dB nHL click stimuli or in no-stimulus conditions. In each condition, 10,000 individual sweeps of 20 ms duration were stored off-line for lab analysis. Data was acquired via a Neuroscan "Synamps" amplifier and Scan acquisition software, data was digitized at 10k Hz and filtered from 100 to 3000 Hz.

Figure 4:
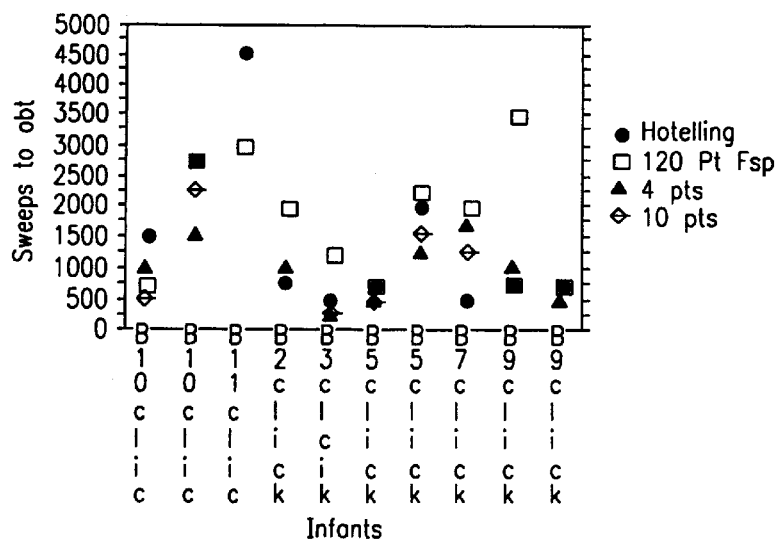
FIG. 4 is a data plot comparing performance of the present invention with prior art $F_{SP}$ and another type new of analysis.
Figure 5:
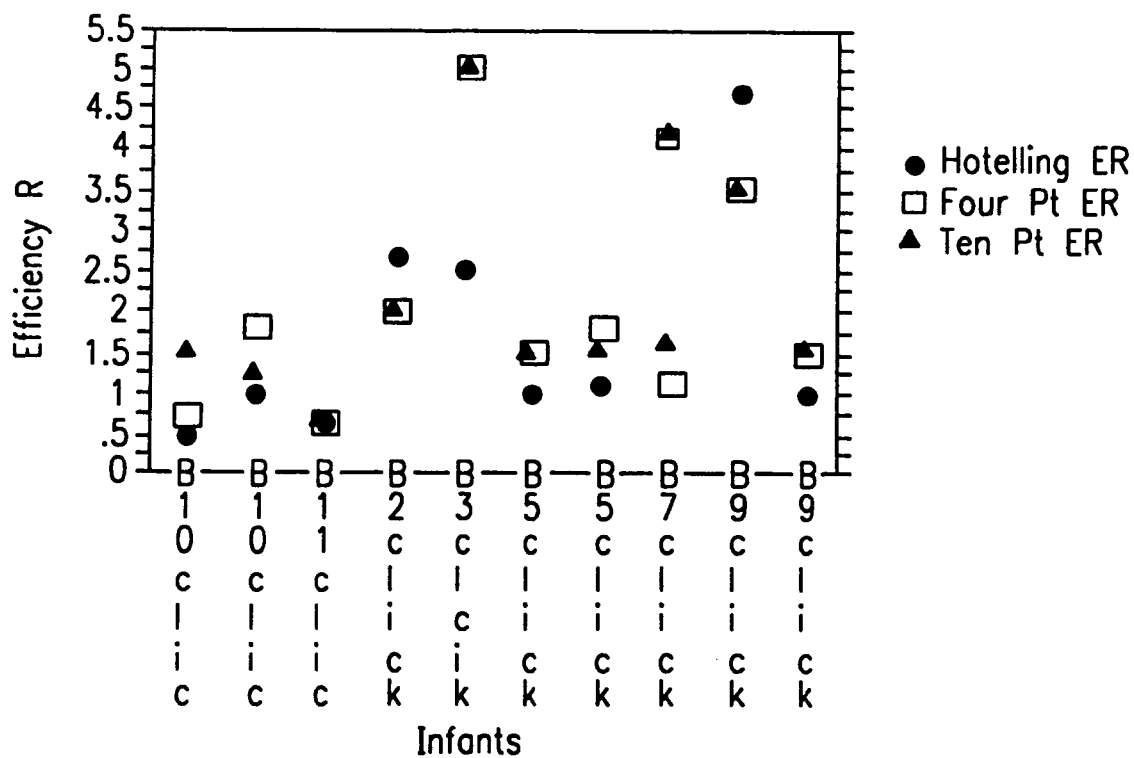
FIG. 5 is a data plot comparing efficiency of the present invention with prior art $F_{SP}$ and another new type of analysis.

Electrophysiologic recordings with click stimuli were analyzed with the present invention, with another algorithm d (a Point-Optimized Variance Ratio (POVR), which is a modified $F_{SP}$ technique) and with standard $F_{SP}$. Probability curves were constructed for each set of data using standard (120 pt) $F_{SP}$, POVR with 4 and 10-point selections and Hotelling $T^2$. The intersection of $-\log_{10} p=2$ revealed the number of sweeps necessary in each condition to reach alpha of 0.01. Those data are plotted in FIG. 4. A significant reduction in the number of sweeps was found for both the POVR and Hotelling algorithms when compared to standard $F_{SP}$. Efficiency ratios (#sweeps in standard $F_{SP}$ condition/# sweeps in test condition) for 3 tests are shown in a scatter-plot on FIG. 5.

The 120-point (standard) $F_{SP}$ can be considered as a baseline against which to evaluate the invention. It should be noted that each set of measurements in a given baby constitutes an element of a random sample of possible observed values of the statistics. Thus, fluctuation in the numbers of sweeps required, and differences from case to case in the relationships between the statistics, are to be expected. Relative to the 120-point $F_{SP}$ baseline, the invention improves the efficiency of measurement in all cases except case B11clickr. In several cases, the improvement is dramatic (such as for B9clickl). Such a result may well make the difference as to whether any valid screening result at all could be obtained practically in such a case. In general, the gains are expressed by the average values of the efficiency ratios, which are very favorable.

The present invention has been described in the context of a screening process utilizing auditory brainstem response (ABR). Another physiologic measure currently in use for evaluation of hearing status in newborn infants is otoacoustic emissions (OAE). Screening techniques using this measure have been shown to be fast and reasonably accurate in identifying hearing impairment in newborns. As with ABR, OAE is amenable to objective response detection and automation. The detection algorithms described herein could also be applied to OAE with only minor modifications.

It will be recognized that the above described invention may be embodied in other specific forms without departing from the spirit or essential characteristics of the disclosure. Thus, it is understood that the invention is not to be limited by the foregoing illustrative details, but rather is to be defined by the appended claims.

What is claimed is:

1. A method for gathering and analyzing ABR signal data generated in response to auditory stimuli to determine hearing capacity of an individual comprising the steps of:
    (a) generating a plurality of auditory stimuli;
    (b) presenting said auditory stimuli to a test subject's ear;
    (c) collecting electrophysiologic signal data from the test subject within a time window following said each of a specified number of auditory stimuli;
    (d) computing a cumulative test subject average waveform from said collected electrophysiologic signal data;
    (e) computing a Hotelling $T^2$ statistic for said cumulative test subject average waveform;
    (f) computing a probability value associated with said computed Hotelling $T^2$ statistic;
    (g) repeating steps (a) through (f) adding to the cumulative test subject average waveform if said computed probability value exceeds a predetermined threshold and declaring that the test subject responded to the auditory stimulus if the computed probability value is below said predetermined threshold; and
    (h) terminating steps (a) through (f) and declaring that no response is present if a predetermined number of stimuli have been presented without the computed probability value falling below the predetermined threshold.

2. The method of claim 1 wherein said Hotelling $T^2$ statistic has the form:

$$\frac{N-k}{k(N-1)} \cdot N(\bar{x} - \mu_0)' S^{-1} (\bar{x} - \mu_0)$$

where
    N is a number of times step (c) is repeated;
    k is a number of selected test points;
    $\bar{x}$ is an average data vector for said k test points;
    $\mu_o$ is a population mean vector; and
    $S^{-1}$ is the inverse of a k×k covariance matrix.

3. A system for gathering and analyzing ABR signal data generated in response to auditory stimuli to determine hearing capacity of an individual comprising:
    (a) means for generating a plurality of auditory stimuli;
    (b) means for presenting said auditory stimuli to a test subject's ear;
    (c) means for collecting electrophysiologic signal data from the test subject within a time window following each of a specified number of said auditory stimuli;
    (d) means for computing a cumulative test subject ABR waveform from collected electrophysiologic signal data;
    (e) means for computing a Hotelling $T^2$ statistic for accumulative test subject average waveform;
    (f) means for computing probability value associated with a computed Hotelling $T^2$ statistic;
    (g) means for iteratively operating (a) through (f) adding to the cumulative test subject average waveform if said computed probability value exceeds a predetermined threshold and declaring that the test subject responded to the auditory stimulus if the computed probability value is below said predetermined threshold; and
    (h) means for terminating operation of (a) through (f) and declaring that no response is present if a predetermined number of stimuli have been presented without the computed probability value falling below the predetermined threshold.

4. The system of claim 3 wherein said Hotelling $T^2$ statistic has the form:

$$\frac{N-k}{k(N-1)} \cdot N(\bar{x} - \mu_0)' S^{-1} (\bar{x} - \mu_0)$$

where
    N is a number of times electrophysiologic signal data is collected;
    k is a number of selected test points;
    $\bar{x}$ is an average data vector for said k test points;
    $\mu_o$ is a population mean vector; and
    $S^{-1}$ is the inverse of a k×k covariance matrix.

* * * * *

UNITED STATES PATENT AND TRADEMARK OFFICE
CERTIFICATE OF CORRECTION

PATENT NO. : 6,200,273 B1
DATED : March 13, 2001
INVENTOR(S) : Sininger et al.

It is certified that error appears in the above-identified patent and that said Letters Patent is hereby corrected as shown below:

<u>Column 12, claim 3,</u>
Line 12, delete "accumulative" and insert -- a cumulative --.

Signed and Sealed this

Ninth Day of April, 2002

Attest:

JAMES E. ROGAN
*Attesting Officer*  *Director of the United States Patent and Trademark Office*